(12) United States Patent
Miller et al.

(10) Patent No.: US 11,441,104 B2
(45) Date of Patent: *Sep. 13, 2022

(54) AQUEOUS CLEANING FORMULATION

(71) Applicants: Dow Global Technologies LLC, Midland, MI (US); Rohm and Haas Company, Collegeville, PA (US)

(72) Inventors: Daniel S. Miller, Phoenixville, PA (US); Andrea C. Keenan, Pottstown, PA (US); Scott Backer, Phoenixville, PA (US); Edward D. Daugs, Midland, MI (US); Christopher J. Tucker, Midland, MI (US); Robert Butterick, Swedesboro, NJ (US)

(73) Assignees: Dow Global Technologies, Midland, MI (US); Rohm and Haas, Collegeville, PA (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/970,971

(22) PCT Filed: Mar. 14, 2019

(86) PCT No.: PCT/US2019/022221
§ 371 (c)(1),
(2) Date: Aug. 19, 2020

(87) PCT Pub. No.: WO2019/194947
PCT Pub. Date: Oct. 10, 2019

(65) Prior Publication Data
US 2021/0009923 A1    Jan. 14, 2021

Related U.S. Application Data

(60) Provisional application No. 62/652,388, filed on Apr. 4, 2018.

(51) Int. Cl.
| | | |
|---|---|---|
| C11D 3/37 | (2006.01) | |
| C11D 3/20 | (2006.01) | |
| C11D 1/72 | (2006.01) | |
| C11D 3/33 | (2006.01) | |
| C11D 3/43 | (2006.01) | |
| C11D 3/50 | (2006.01) | |

(52) U.S. Cl.
CPC .............. *C11D 3/2093* (2013.01); *C11D 1/72* (2013.01); *C11D 3/2068* (2013.01); *C11D 3/33* (2013.01); *C11D 3/43* (2013.01); *C11D 3/50* (2013.01)

(58) Field of Classification Search
CPC ....... A61K 2300/00; A61K 47/44; A61K 8/86
See application file for complete search history.

(56) References Cited

U.S. PATENT DOCUMENTS

| | | | |
|---|---|---|---|
| 4,250,165 A | 2/1981 | Foley | |
| 4,921,694 A | 5/1990 | Hoppe et al. | |
| 5,051,212 A | 9/1991 | Culshaw et al. | |
| 5,374,614 A | 12/1994 | Behan et al. | |
| 5,736,505 A | 4/1998 | Manzo et al. | |
| 6,280,533 B1 * | 8/2001 | Hoppe ................. | B09C 1/02 134/26 |
| 6,383,995 B1 | 5/2002 | Maurin et al. | |
| 6,489,285 B2 | 12/2002 | Faber | |
| 7,202,200 B1 | 4/2007 | DeLeo et al. | |
| 7,368,135 B1 | 5/2008 | Anderson | |
| 8,048,836 B2 | 11/2011 | Molenda et al. | |
| 8,222,196 B2 | 7/2012 | Smith et al. | |
| 8,287,841 B2 | 10/2012 | Nguyen et al. | |
| 8,613,939 B2 | 12/2013 | Dobkowski | |
| 2012/0015857 A1 | 1/2012 | Chen et al. | |
| 2015/0017214 A1 | 1/2015 | Warr et al. | |
| 2020/0353113 A1 * | 11/2020 | Mui ................. | A61K 8/86 |

FOREIGN PATENT DOCUMENTS

| | | |
|---|---|---|
| EP | 2940114 | 11/2015 |
| JP | 2011038030 | 2/2011 |
| WO | 2012054465 | 4/2012 |

OTHER PUBLICATIONS

Clairman., "Amended Safety Assessment of PEGylated Oils as Used in Cosmetics." 2012, p. 0-29.
Sibilia., "A Guide to Materials and Characterization and Chemical Analysis." 1988, p. 81-84.

* cited by examiner

*Primary Examiner* — John R Hardee
(74) *Attorney, Agent, or Firm* — Thomas S. Deibert

(57) ABSTRACT

An aqueous cleaning formulation is provided including a water; an essential oil, wherein the essential oil is selected from the group consisting of lavender oil, rosemary oil, thyme oil and mixtures thereof; a derivative of castor oil having a formula selected from formula I and formula II; an ethoxylated phenol having formula III; and a cleaning surfactant.

10 Claims, No Drawings

AQUEOUS CLEANING FORMULATION

The present invention relates to an aqueous cleaning formulation. In particular, the present invention relates to an aqueous cleaning formulation including a water; an essential oil, wherein the essential oil is selected from the group consisting of lavender oil, rosemary oil, thyme oil and mixtures thereof; a derivative of castor oil having a formula selected from formula I and formula II; an ethoxylated phenol having formula III; and a cleaning surfactant.

Aqueous cleaning compositions, for example, floor care formulations, hard surface cleaning formulations and personal care formulations have a wide array of uses. For example, use cleaning hard surfaces such as floors, counters, walls, tables, and other things made of, for example, wood, stone, laminate, ceramic and plastic materials which need to be cleaned periodically of accumulated dirt, oil, grease, and other contaminants.

Aqueous cleaning compositions typically include at least one detergent surfactant for cleaning effectiveness. Aqueous cleaning compositions also commonly include fragrances. While certain essential oil based fragrances offer a pleasant odor that would be desirable for incorporation in such aqueous cleaning compositions, nevertheless prove unacceptable from a formulation perspective. Specifically, the primarily hydrophobic nature of essential oil based fragrances makes sufficient solubilization of these molecules in aqueous, surfactant containing formulations, challenging. Poorly solubilized fragrances can cause formulation instability leading to, inter alia, undesired phase separation.

A variety of conventional hard surface cleaning formulations have been disclosed, for example, a hard surface cleaner containing alkyl polyglycosides for hard surface cleaning is disclosed by Faber in U.S. Pat. No. 6,489,285. Faber discloses a dilutable, non-rinse hard surface cleaner that includes (i) either (a) a combination of a specific nonionic surfactant and a quaternary ammonium surfactant or (b) a combination of a specific nonionic surfactant and an anionic surfactant, (ii) a water soluble glycol ether, (iii) a builder, (iv) d-limonene, and (v) water.

Notwithstanding, there remains a continuing need for effective aqueous cleaning formulations. In particular, there remains a need for an effective aqueous cleaning formulation that provides cleaning action, a pleasant fragrance and formulational stability.

The present invention provides an aqueous cleaning formulation, comprising: a water; an essential oil, wherein the essential oil comprises 50 to 100 wt % of one organic component; a derivative of castor oil having a formula selected from formula I and formula II

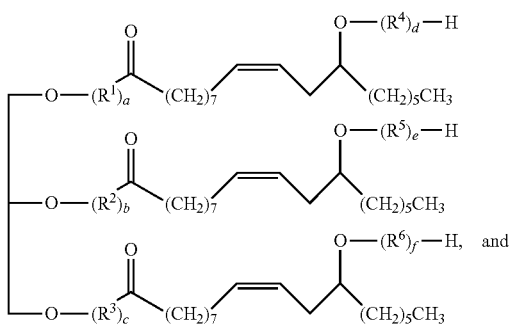

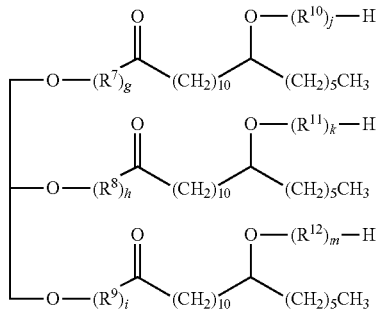

wherein $R^1$, $R^2$, $R^3$, $R^4$, $R^5$, $R^6$, $R^7$, $R^8$, $R^9$, $R^{10}$, $R^{11}$ and $R^{12}$ are each independently selected from the group consisting of a —$CH_2CH_2O$— group, a —$CH_2CH_2CH_2O$— group, a —$CH_2CH_2CH_2CH_2O$— group, a —$CH(CH_3)CH_2O$— group, a —$CH_2CH(CH_3)O$— group, a —$CH(CH_3)CH_2CH_2O$— group, a —$CH_2CH(CH_3)$ $CH_2O$— group and a —$CH_2CH_2CH(CH_3)O$— group each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250; an ethoxylated phenol having formula III

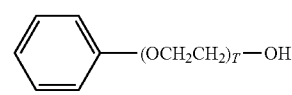

wherein T is an average of 3 to 8; and a cleaning surfactant.

The present invention provides an aqueous cleaning formulation, comprising: 10 to 99 wt %, based on the weight of the aqueous cleaning formulation, of a water; an essential oil, wherein the essential oil is selected from the group consisting of lavender oil, rosemary oil, thyme oil, d-limonene, α-pinene and mixtures thereof; 0.01 to 25 wt %, based on the weight of the aqueous cleaning formulation, of a derivative of castor oil having a formula selected from formula I and formula II; wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250; 0.01 to 30 wt %, based on the weight of the aqueous cleaning formulation, of an ethoxylated phenol having formula III; wherein T is an average of 3 to 8; 0.1 to 15 wt %, based on weight of the aqueous cleaning formulation, of a cleaning surfactant, wherein the cleaning surfactant includes a non-ionic surfactant; 0.1 to 20 wt %, based on the weight of the aqueous cleaning formulation, of a chelating agent; 0.1 to 10 wt %, based on the weight of the aqueous cleaning formulation, of a hydrotrope; and 0.01 to 10 wt %, based on the weight of the aqueous cleaning formulation, of an organic solvent.

The present invention provides an aqueous cleaning formulation, comprising: 10 to 99 wt %, based on the weight of the aqueous cleaning formulation, of a water; 7.6 to 10 wt %, based on the weight of the aqueous cleaning formulation, of the essential oil, wherein the essential oil is lavender oil; 0.01 to 25 wt %, based on the weight of the aqueous cleaning formulation, of a derivative of castor oil having a formula selected from formula I and formula II; wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250; 0.01 to 30 wt %, based on the weight of the aqueous cleaning formulation, of an ethoxylated phenol having formula III; wherein T is an average of 3 to 8; 0.1 to 15 wt %, based on weight of the aqueous cleaning formulation, of a cleaning surfactant, wherein the cleaning surfactant includes a non-ionic surfactant; 0.1 to 20 wt %, based on the weight of the aqueous cleaning formulation, of a chelating agent; 0.1 to 10 wt %, based on the weight of the aqueous cleaning formulation, of a hydrotrope; and 0.01 to 10 wt %, based on the weight of the aqueous cleaning formulation, of an organic solvent.

The present invention provides an aqueous cleaning formulation, comprising: 10 to 99 wt %, based on the weight of the aqueous cleaning formulation, of a water; 0.61 to 1 wt %, based on the weight of the aqueous cleaning formulation, of the essential oil, wherein the essential oil is rosemary oil; 0.01 to 25 wt %, based on the weight of the aqueous cleaning formulation, of a derivative of castor oil having a formula selected from formula I and formula II; wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250; 0.01 to 30 wt %, based on the weight of the aqueous cleaning formulation, of an ethoxylated phenol having formula III; wherein T is an average of 3 to 8; 0.1 to 15 wt %, based on weight of the aqueous cleaning formulation, of a cleaning surfactant, wherein the cleaning surfactant includes a non-ionic surfactant; 0.1 to 20 wt %, based on the weight of the aqueous cleaning formulation, of a chelating agent; 0.1 to 10 wt %, based on the weight of the aqueous cleaning formulation, of a hydrotrope; and 0.01 to 10 wt %, based on the weight of the aqueous cleaning formulation, of an organic solvent.

The present invention provides an aqueous cleaning formulation, comprising: 10 to 99 wt %, based on the weight of the aqueous cleaning formulation, of a water; 5 to 10 wt%, based on the weight of the aqueous cleaning formulation, of the essential oil, wherein the essential oil is thyme oil; 0.01 to 25 wt %, based on the weight of the aqueous cleaning formulation, of a derivative of castor oil having a formula selected from formula I and formula II; wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250; 0.01 to 30 wt %, based on the weight of the aqueous cleaning formulation, of an ethoxylated phenol having formula III; wherein T is an average of 3 to 8; 0.1 to 15 wt %, based on weight of the aqueous cleaning formulation, of a cleaning surfactant, wherein the cleaning surfactant includes a non-ionic surfactant; 0.1 to 20 wt %, based on the weight of the aqueous cleaning formulation, of a chelating agent; 0.1 to 10 wt %, based on the weight of the aqueous cleaning formulation, of a hydrotrope; and 0.01 to 10 wt %, based on the weight of the aqueous cleaning formulation, of an organic solvent.

DETAILED DESCRIPTION

The aqueous cleaning formulations of the present invention provide cleaning action and a pleasant fragrance, wherein the aqueous cleaning formulation remains stable with a high fragrance loading, wherein the fragrance is an otherwise difficult to stably incorporate essential oil based fragrance.

Unless otherwise indicated, ratios, percentages, parts, and the like are by weight. Weight percentages (or wt %) in the composition are percentages of dry weight, i.e., excluding any water that may be present in the composition. Percentages of monomer units in the polymer are percentages of solids weight, i.e., excluding any water present in a polymer emulsion.

As used herein, unless otherwise indicated, the terms "weight average molecular weight" and "Mw" are used interchangeably to refer to the weight average molecular weight as measured in a conventional manner with gel permeation chromatography (GPC) and conventional standards, such as polyethylene glycol standards. GPC techniques are discussed in detail in Modem Size Exclusion Chromatography, W. W. Yau, J. J. Kirkland, D. D. Bly; Wiley-Interscience, 1979, and in A Guide to Materials Characterization and Chemical Analysis, J. P. Sibilia; VCH, 1988, p. 81-84. Weight average molecular weights are reported herein in units of Daltons.

Preferably, the aqueous cleaning formulation of the present invention is selected from the group consisting of a floor care formulation, a hard surface cleaning formulation and a personal care formulation. More preferably, the aqueous cleaning formulation of the present invention is selected from the group consisting of a floor care formulation and a hard surface cleaning formulation. Most preferably, the aqueous cleaning formulation of the present invention is a floor care formulation.

Preferably, the aqueous cleaning formulation of the present invention, comprises: water (preferably, 10 to 99 wt % (more preferably, 25 to 98 wt %; most preferably, 50 to 97 wt %), based on the weight of the aqueous cleaning formulation, of the water); an essential oil (preferably, 0.5 to 10 wt %, based on the weight of the aqueous cleaning formulation, of the essential oil), wherein the essential oil comprises 50 to 100 wt % of one organic component (preferably, wherein the essential oil is selected from the group consisting of lavender oil, rosemary oil, thyme oil, d-limonene, α-pinene and mixtures thereof); a derivative of castor oil (preferably, 0.01 to 25 wt % (more preferably, 0.05 to 10 wt %; still more preferably, 0.1 to 5 wt %; most preferably, 1 to 3 wt %), based on the weight of the aqueous cleaning formulation, of the derivative of castor oil) having a formula selected from formula I and formula II

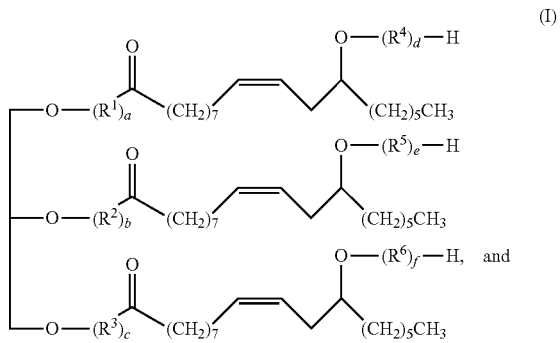

-continued

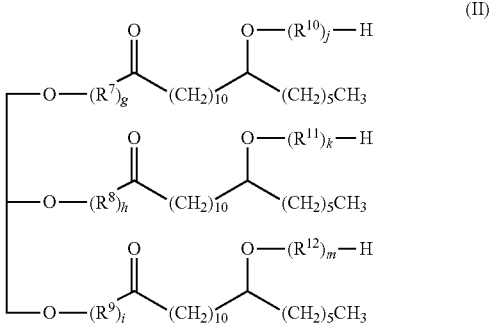
(II)

wherein $R^1, R^2, R^3, R^4, R^5, R^6, R^7, R^8, R^9, R^{10}, R^{11}$, and $R^{12}$ are each independently selected from a —$CH_2CH_2O$— group, a —$CH_2CH_2CH_2O$— group, a —$CH_2CH_2CH_2CH_2O$— group,
a —$CH(CH_3)CH_2O$— group, a —$CH_2CH(CH_3)O$— group, a —$CH(CH_3)CH_2CH_2O$— group,
a —$CH_2CH(CH_3)CH_2O$— group and a —$CH_2CH_2CH(CH_3)O$— group (preferably,
a —$CH_2CH_2O$— group and a —$CH_2CH_2CH_2O$— group; more preferably, a —$CH_2CH_2O$— group); wherein a, b, c, d, e, f g, h, i, j, k and m are each independently a number of 0 to 250; wherein the average sum of a+b+c+d+e+f is 1 to 250 (preferably, 5 to 200; more preferably, 15 to 100; most preferably, 30 to 60); wherein the average sum of g+h+i+j+k+m is 1 to 250 (preferably, 5 to 200; more preferably, 15 to 100; most preferably, 30 to 60); an ethoxylated phenol (preferably, 0.01 to 30 wt % (more preferably, 0.1 to 20 wt %; still more preferably, 1 to 10 wt %; most preferably, 2.5 to 7.5 wt %), based on the weight of the aqueous cleaning formulation, of the ethoxylated phenol) having formula III

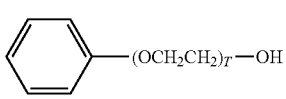
(III)

wherein T is an average of 3 to 8 (preferably, 3.25 to 7.5; more preferably, 3.5 to 7; still more preferably, 3.75 to 6.75; most preferably, 3.9 to 6.5); and a cleaning surfactant (preferably, 0.01 to 30 wt % (more preferably, 1 to 25 wt %; still more preferably, 5 to 20 wt %; most preferably, 7.5 to 15 wt %), based on the weight of the aqueous cleaning formulation, of the cleaning surfactant)).

Preferably, the aqueous cleaning formulation of the present invention, comprises: 10 to 99 wt % (more preferably, 25 to 98 wt %; most preferably, 50 to 97 wt %), based on the weight of the aqueous cleaning formulation, of a water. Preferable, the aqueous cleaning formulation of the present invention, comprises 10 to 99 wt % (more preferably, 25 to 98 wt %; most preferably, 50 to 97 wt %), based on the weight of the aqueous cleaning formulation, of a water, wherein the water is at least one of distilled water, deionized water and industrial soft water. More preferably, the aqueous cleaning formulation of the present invention, comprises 10 to 99 wt % (more preferably, 25 to 98 wt %; most preferably, 50 to 97 wt %), based on the weight of the aqueous cleaning formulation, of a water, wherein the water is distilled and deionized. Most preferably, the aqueous cleaning formulation of the present invention, comprises 10 to 99 wt % (more preferably, 25 to 98 wt %; most preferably, 50 to 97 wt %), based on the weight of the aqueous cleaning formulation, of a water, wherein the water is distilled, deionized and industrial soft to avoid introduction of undesirable metal ions to the aqueous cleaning formulation.

Preferably, the aqueous cleaning formulation of the present invention, comprises: 0.5 to 10 wt %, based on the weight of the aqueous cleaning formulation, of an essential oil, wherein the essential oil comprises 50 to 100 wt % of one organic component (preferably, wherein the essential oil is selected from the group consisting of lavender oil, rosemary oil, thyme oil, d-limonene, α-pinene and mixtures thereof). Preferably, the essential oil used in the aqueous cleaning formulation, comprises at least one of lavender oil, rosemary oil, thyme oil, d-limonene and α-pinene. Preferably, the essential oil used in the aqueous cleaning formulation of the present invention, includes lavender oil. Preferably, the essential oil used in the aqueous cleaning formulation of the present invention, includes rosemary oil. Preferably, the essential oil used in the aqueous cleaning formulation of the present invention, includes thyme oil. Preferably, the essential oil used in the aqueous cleaning formulation of the present invention, includes d-limonene. Preferably, the essential oil used in the aqueous cleaning formulation of the present invention, includes α-pinene. More preferably, the essential oil used in the aqueous cleaning formulation of the present invention is lavender oil. More preferably, the essential oil used in the aqueous cleaning formulation of the present invention is rosemary oil. More preferably, the essential oil used in the aqueous cleaning formulation of the present invention is thyme oil. Preferably, the essential oil used in the aqueous cleaning formulation of the present invention, is d-limonene. Preferably, the essential oil used in the aqueous cleaning formulation of the present invention, is α-pinene.

Preferably, the aqueous cleaning formulation of the present invention, comprises 7.6 to 10 wt % (more preferably, 7.75 to 10 wt %; most preferably, 8 to 10 wt %), based on the weight of the aqueous cleaning formulation, of an essential oil, wherein the essential oil is lavender oil. Preferably, wherein the lavender oil contains eight organic components each comprising at least 1.0 wt % of the lavender oil and wherein the lavender oil contains 50 to 60 wt % of one of the eight organic components (i.e., benxyl benzoate).

Preferably, the essential oil used in the aqueous cleaning formulation of the present invention, comprises 0.61 to 1 wt % (more preferably, 0.7 to 0.85 wt %; most preferably, 0.75 to 0.8 wt %), based on the weight of the aqueous cleaning formulation, of an essential oil, wherein the essential oil is rosemary oil. Preferably, wherein the rosemary oil contains six organic components each comprising at least 1.0 wt % of the rosemary oil and wherein the rosemary oil contains 70 to 80 wt % of one of the six organic components (i.e., diethyl hexyl phthalate).

Preferably, the essential oil used in the aqueous cleaning formulation of the present invention, comprises 5 to 10 wt % (more preferably, 6 to 8 wt %; most preferably, 6.5 to 7 wt %), based on the weight of the aqueous cleaning formulation, of an essential oil, wherein the essential oil is thyme oil. Preferably, wherein the thyme oil contains four organic components each comprising at least 0.5 wt % of the thyme oil and wherein the thyme contains 55 to 65 wt % of one of the eight organic components (i.e., thymol).

Preferably, the essential oil used in the aqueous cleaning formulation of the present invention, comprises 0.5 to 10 wt %, based on the weight of the aqueous cleaning formulation, of an essential oil, wherein the essential oil is D-limonene.

Preferably, wherein the D-limonene contains at least one organic component and wherein the D-limonene contains at least 90 wt % of the at least one organic components (i.e., d-limonene).

Preferably, the essential oil used in the aqueous cleaning formulation of the present invention, comprises 0.5 to 10 wt %, based on the weight of the aqueous cleaning formulation, of an essential oil, wherein the essential oil is α-pinene. Preferably, wherein the α-pinene contains at least one organic component and wherein the α-pinene contains at least 90 wt % of the at least one organic components (i.e., α-pinene).

Preferably, the aqueous cleaning formulation of the present invention, comprises: 0.01 to 25 wt % (more preferably, 0.05 to 10 wt %; still more preferably, 0.1 to 5 wt %; most preferably, 1 to 3 wt %), based on the weight of the aqueous cleaning formulation, of a derivative of castor oil having a formula selected from formula I and formula II, wherein $R^1$, $R^2$, $R^3$, $R^4$, $R^5$, $R^6$, $R^7$, $R^8$, $R^9$, $R^{10}$, $R^{11}$, and $R^{12}$ are each independently selected from
a —CH$_2$CH$_2$O— group, a —CH$_2$CH$_2$CH$_2$O— group, a —CH$_2$CH$_2$CH$_2$CH$_2$O— group,
a —CH(CH$_3$)CH$_2$O— group, a —CH$_2$CH(CH$_3$)O— group,
a —CH(CH$_3$)CH$_2$CH$_2$O— group,
a —CH$_2$CH(CH$_3$)CH$_2$O— group and a —CH$_2$CH$_2$CH (CH$_3$)O— group (preferably,
a —CH$_2$CH$_2$O— group and a —CH$_2$CH$_2$CH$_2$O— group; more preferably, a —CH$_2$CH$_2$O— group); wherein a, b, c, d, e, f, g, h, i, j, k and m are each independently a number of 0 to 250; wherein the average sum of a+b+c+d+e+f is 1 to 250 (preferably, 5 to 200; more preferably, 15 to 100; most preferably, 30 to 60); wherein the average sum of g+h+i+ j+k+m is 1 to 250 (preferably, 5 to 200; more preferably, 15 to 100; most preferably, 20 to 60).

Preferably, the aqueous cleaning formulation of the present invention, comprises: 0.01 to 25 wt % (more preferably, 0.05 to 10 wt %; still more preferably, 0.1 to 5 wt %; most preferably, 1 to 3 wt %), based on the weight of the aqueous cleaning formulation, of a derivative of castor oil having a formula selected from formula I and formula II, wherein the derivative of castor oil is selected from the group consisting of a polyethylene glycol derivative of hydrogenated castor oil, a polyethylene glycol derivative of castor oil and blends thereof. More preferably, the aqueous cleaning formulation of the present invention, comprises: 0.01 to 25 wt % (more preferably, 0.05 to 10 wt %; still more preferably, 0.1 to 5 wt %; most preferably, 1 to 3 wt %), based on the weight of the aqueous cleaning formulation, of a derivative of castor oil having a formula selected from formula I and formula II, wherein the derivative of castor oil is selected from the group consisting of a PEG-5 hydrogenated castor oil, a PEG-5 castor oil, a PEG-7 hydrogenated castor oil, a PEG-7 castor oil, a PEG-16 hydrogenated castor oil, a PEG-16 castor oil, a PEG-25 hydrogenated castor oil, a PEG-25 castor oil, a PEG-30 hydrogenated castor oil, a PEG-30 castor oil, a PEG-40 hydrogenated castor oil, a PEG-40 castor oil, a PEG-60 hydrogenated castor oil, a PEG-60 castor oil, a PEG-100 hydrogenated castor oil, a PEG-100 castor oil, a PEG-200 hydrogenated castor oil, a PEG-200 castor oil and blends thereof. Still more preferably, the aqueous cleaning formulation of the present invention, comprises: 0.01 to 25 wt % (more preferably, 0.05 to 10 wt %; still more preferably, 0.1 to 5 wt %; most preferably, 1 to 3 wt %), based on the weight of the aqueous cleaning formulation, of a derivative of castor oil having a formula selected from formula I and formula II, wherein the derivative of castor oil is selected from the group consisting of PEG-40 hydrogenated castor oil, PEG-20 castor oil and blends thereof. Most preferably, the aqueous cleaning formulation of the present invention, comprises: 0.01 to 25 wt % (more preferably, 0.05 to 10 wt %; still more preferably, 0.1 to 5 wt %; most preferably, 1 to 3 wt %), based on the weight of the aqueous cleaning formulation, of a derivative of castor oil having a formula selected from formula I and formula II, wherein the derivative of castor oil is selected from the group consisting of a PEG-40 hydrogenated castor oil and a PEG-20 castor oil.

Preferably, the aqueous cleaning formulation of the present invention, comprises: 0.01 to 30 wt % (preferably, 0.1 to 20 wt %; more preferably, 1 to 10 wt %; most preferably, 2.5 to 7.5 wt %), based on the weight of the aqueous cleaning formulation, of an ethoxylated phenol having formula III

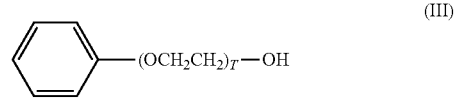

wherein T is an average of 3 to 8. More preferably, the aqueous cleaning formulation of the present invention, comprises: 0.01 to 30 wt % (preferably, 0.1 to 20 wt %; more preferably, 1 to 10 wt %; most preferably, 2.5 to 7.5 wt %), based on the weight of the aqueous cleaning formulation, of an ethoxylated phenol having formula III; wherein T is an average of 3.25 to 7.5. Still more preferably, the aqueous cleaning formulation of the present invention, comprises: 0.01 to 30 wt % (preferably, 0.1 to 20 wt %; more preferably, 1 to 10 wt %; most preferably, 2.5 to 7.5 wt %), based on the weight of the aqueous cleaning formulation, of an ethoxylated phenol having formula III; wherein T is an average of 3.5 to 7. Yet still more preferably, the aqueous cleaning formulation of the present invention, comprises: 0.01 to 30 wt % (preferably, 0.1 to 20 wt %; more preferably, 1 to 10 wt %; most preferably, 2.5 to 7.5 wt %), based on the weight of the aqueous cleaning formulation, of an ethoxylated phenol having formula III; wherein T is an average of 3.75 to 6.75. Most preferably, the aqueous cleaning formulation of the present invention, comprises: 0.01 to 30 wt % (preferably, 0.1 to 20 wt %; more preferably, 1 to 10 wt %; most preferably, 2.5 to 7.5 wt %), based on the weight of the aqueous cleaning formulation, of an ethoxylated phenol having formula III; wherein T is an average of 3.9 to 6.5.

Preferably, the aqueous cleaning formulation of the present invention, comprises: 0.01 to 30 wt % (more preferably, 1 to 25 wt %; still more preferably, 5 to 20 wt %; most preferably, 7.5 to 15 wt %), based on the weight of the aqueous cleaning formulation, of a cleaning surfactant. Cleaning surfactants are selected from the group consisting of anionic surfactants, nonionic surfactants, cationic surfactants, amphoteric surfactants and mixtures thereof.

Anionic surfactants used in the aqueous cleaning formulation of the present invention include alkyl sulfates, alkyl benzene sulfates, alkyl benzene sulfonic acids, alkyl benzene sulfonates, alkyl polyethoxy sulfates, alkoxylated alcohols, paraffin sulfonic acids, paraffin sulfonates, olefin sulfonic acids, olefin sulfonates, alpha-sulfocarboxylates, esters of alpha-sulfocarboxylates, alkyl glyceryl ether sulfonic acids, alkyl glyceryl ether sulfonates, sulfates of fatty acids, sulfonates of fatty acids, sulfonates of fatty acid esters, alkyl phenols, alkyl phenol polyethoxy ether sulfates, 2-acryloxy-alkane-1-sulfonic acid, 2-acryloxy-alkane-1-sulfonate, beta-alkyloxy alkane sulfonic acid, beta-alkyloxy alkane sulfonate, amine oxides and mixtures thereof. Preferred anionic surfactants include $C_{8-20}$ alkyl benzene sulfates, $C_{8-20}$ alkyl benzene sulfonic acid, $C_{8-20}$ alkyl benzene sulfonate, paraffin sulfonic acid, paraffin sulfonate, alpha-olefin sulfonic acid, alpha-olefin sulfonate, alkoxylated alcohols, $C_{8-20}$ alkyl phenols, amine oxides, sulfonates of fatty acids, sulfonates of fatty acid esters and mixtures thereof. More preferred cleaning surfactants include $C_{12-16}$ alkyl benzene sulfonic acid, $C_{12-16}$ alkyl benzene sulfonate, $C_{12-18}$ paraffin-sulfonic acid, $C_{12-18}$ paraffin-sulfonate and mixtures thereof.

Preferably, the aqueous cleaning formulation of the present invention, comprises: 0 to 30 wt % (more preferably, 0.1 to 15 wt %; most preferably, 0.5 to 5 wt %), based on the weight of the aqueous cleaning formulation, of an anionic surfactant. More preferably, the aqueous cleaning formulation of the present invention, comprises: 0 to 30 wt % (more preferably, 0.1 to 15 wt %; most preferably, 0.5 to 5 wt %), based on the weight of the aqueous cleaning formulation, of an anionic cleaning surfactant; wherein the anionic surfactant includes at least one of an alkyl benzene sulfonic acid and an alkyl benzene sulfonate. Still more preferably, the aqueous cleaning formulation of the present invention, comprises: 0 to 30 wt % (more preferably, 0.1 to 15 wt %; most preferably, 0.5 to 5 wt %), based on the weight of the aqueous cleaning formulation, of an anionic cleaning surfactant; wherein the anionic surfactant includes at least one of a $C_{8-20}$ alkyl benzene sulfonic acid and a $C_{8-20}$ alkyl benzene sulfonate. Most preferably, the aqueous cleaning formulation of the present invention, comprises: 0 to 30 wt % (more preferably, 0.1 to 15 wt %; most preferably, 0.5 to 5 wt %), based on the weight of the aqueous cleaning formulation, of an anionic surfactant; wherein the anionic surfactant includes at least one of dodecyl benzene sulfonic acid and dodecyl benzene sulfonate.

Non-ionic surfactants used in the aqueous cleaning formulation of the present invention include alkoxylates (e.g., polyglycol ethers, fatty alcohol polyglycol ethers, alkylphenol polyglycol ethers, end group capped polyglycol ethers, mixed ethers, hydroxy mixed ethers, fatty acid polyglycol esters and mixtures thereof. Preferred non-ionic surfactants include fatty alcohol polyglycol ethers. More preferred non-ionic surfactants include secondary alcohol ethoxylates, ethoxylated 2-ethylhexanol, ethoxylated seed oils, butanol caped ethoxylated 2-ethylhexanol and mixtures thereof. Most preferred non-ionic surfactants include secondary alcohol ethoxylates.

Preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant. More preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant; wherein the non-ionic surfactant includes an alkoxylate. Still more preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant; wherein the non-ionic surfactant includes at least one of a polyglycol ether, a fatty alcohol polyglycol ether, an alkylphenol polyglycol ether, an end group capped polyglycol ether, a mixed ether, a hydroxy mixed ether and a fatty acid polyglycol ester. Still more preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant; wherein the non-ionic surfactant includes a fatty alcohol polyglycol ether. Yet more preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant; wherein the non-ionic surfactant includes at least one of a secondary alcohol ethoxylate, an ethoxylated 2-ethylhexanol, an ethoxylated seed oil and a butanol caped ethoxylated 2-ethylhexanol. Most preferably, the aqueous cleaning formulation of the present invention, comprises: 0 to 30 wt % (more preferably, 0.1 to 15 wt %; most preferably, 0.5 to 10 wt %), based on the weight of the aqueous cleaning formulation, of a non-ionic surfactant; wherein the non-ionic surfactant includes a secondary alcohol ethoxylates.

Cationic surfactants used in the aqueous cleaning formulation of the present invention include quaternary surface active compounds. Preferred cationic surfactants include quaternary surface active compounds having at least one of an ammonium group, a sulfonium group, a phosphonium group, an iodinium group and an arsonium group. More preferred cationic surfactants include at least one of a dialkyldimethylammonium chloride and alkyl dimethyl benzyl ammonium chloride. Still more preferred cationic surfactants include at least one of $C_{16-18}$ dialkyldimethylammonium chloride, a $C_{8-18}$ alkyl dimethyl benzyl ammonium chloride di-tallow dimethyl ammonium chloride and di-tallow dimethyl ammonium chloride. Most preferred cationic surfactant includes di-tallow dimethyl ammonium chloride.

Preferably, the aqueous cleaning formulation of the present invention, comprises: 0 to 30 wt % (more preferably, 0.01 to 5 wt %; most preferably, 0.5 to 1.5 wt %), based on the weight of the aqueous cleaning formulation, of a cationic surfactant. More preferably, the aqueous cleaning formulation of the present invention, comprises: 0 to 30 wt % (more preferably, 0.01 to 5 wt %; most preferably, 0.5 to 1.5 wt %), based on the weight of the aqueous cleaning formulation, of a cationic surfactant; wherein the cationic surfactant includes at least one quaternary surface active compound having at least one of an ammonium group, a sulfonium group, a phosphonium group, an iodinium group and an arsonium group. Still more preferably, the aqueous cleaning formulation of the present invention, comprises: 0 to 30 wt % (more preferably, 0.01 to 5 wt %; most preferably, 0.5 to 1.5 wt %), based on the weight of the aqueous cleaning formulation, of a cationic surfactant; wherein the cationic surfactant includes at least one of a dialkyldimethylammonium chloride and alkyl dimethyl benzyl ammonium chloride. Still more preferably, the aqueous cleaning formulation of the present invention, comprises: 0 to 30 wt % (more preferably, 0.01 to 5 wt %; most preferably, 0.5 to 1.5 wt %), based on the weight of the aqueous cleaning formulation, of a cationic surfactant; wherein the cationic surfactant includes at least one of $C_{16-18}$ dialkyldimethylammonium chloride, a $C_{8-18}$ alkyl dimethyl benzyl ammonium chloride di-tallow dimethyl ammonium chloride and di-tallow dimethyl ammonium chloride. Most preferably, the aqueous cleaning formulation of the present invention, comprises: 0 to 30 wt % (more preferably, 0.01 to 5 wt %; most preferably, 0.5 to 1.5 wt %), based on the weight of the aqueous cleaning formulation, of a cationic surfactant; wherein the cationic surfactant includes di-tallow dimethyl ammonium chloride.

Amphoteric surfactants used in the aqueous cleaning formulation of the present invention include betaines, amine oxides, alkylamidoalkylamines, alkyl-substituted amine oxides, acylated amino acids, derivatives of aliphatic quaternary ammonium compounds and mixtures thereof. Preferred amphoteric surfactants include derivatives of aliphatic quaternary ammonium compounds. More preferred amphoteric surfactants include derivatives of aliphatic quaternary ammonium compounds with a long chain group having 8 to 18 carbon atoms. Still more preferred amphoteric surfactants include at least one of $C_{12-14}$ alkyldimethylamine oxide, 3-(N,N-dimethyl-N-hexadecyl-ammonio)propane-1-sulfonate, 3-(N,N-dimethyl-N-hexadecylammonio)-2-hydroxypropane-1-sulfonate. Most preferred amphoteric surfactants include at least one of $C_{12-14}$ alkyldimethylamine oxide.

Preferably, the aqueous cleaning formulation of the present invention, comprises: 0 to 30 wt % (more preferably, 0.01 to 20 wt %; still more preferably, 0.1 to 10 wt %; most preferably, 1 to 5 wt %), based on the weight of the aqueous cleaning formulation, of an amphoteric surfactant. More preferably, the aqueous cleaning formulation of the present invention, comprises: 0 to 30 wt % (more preferably, 0.01 to 20 wt %; still more preferably, 0.1 to 10 wt %; most preferably, 1 to 5 wt %), based on the weight of the aqueous cleaning formulation, of an amphoteric surfactant; wherein the amphoteric surfactant includes at least one betaine, amine oxide, alkylamidoalkylamine, alkyl-substituted amine oxide, acylated amino acid and a derivative of an aliphatic quaternary ammonium compound. Still more preferably, the aqueous cleaning formulation of the present invention, comprises: 0 to 30 wt % (more preferably, 0.01 to 20 wt %; still more preferably, 0.1 to 10 wt %; most preferably, 1 to 5 wt %), based on the weight of the aqueous cleaning formulation, of an amphoteric surfactant; wherein the amphoteric surfactant includes a derivative of an aliphatic quaternary ammonium compound. Still more preferably, the aqueous cleaning formulation of the present invention, comprises: 0 to 30 wt % (more preferably, 0.01 to 20 wt %; still more preferably, 0.1 to 10 wt %; most preferably, 1 to 5 wt %), based on the weight of the aqueous cleaning formulation, of an amphoteric surfactant; wherein the amphoteric surfactant includes a derivative of an aliphatic quaternary ammonium compound with a long chain group having 8 to 18 carbon atoms. Most preferably, the aqueous cleaning formulation of the present invention, comprises: 0 to 30 wt % (more preferably, 0.01 to 20 wt %; still more preferably, 0.1 to 10 wt %; most preferably, 1 to 5 wt %), based on the weight of the aqueous cleaning formulation, of an amphoteric surfactant; wherein the amphoteric surfactant includes at least one of $C_{12-14}$ alkyldimethylamine oxide, 3-(N,N-dimethyl-N-hexadecyl-ammonio)propane-1-sulfonate and 3-(N,N-dimethyl-N-hexadecylammonio)-2-hydroxypropane-1-sulfonate.

Preferably, the aqueous cleaning formulation of the present invention, further comprises: 0 to 20 wt % (preferably, 0.1 to 20 wt %; more preferably, 0.5 to 10 wt %; most preferably, 1 to 5 wt %), based on the weight of the aqueous cleaning formulation, of a chelating agent.

Preferably, the aqueous cleaning formulation of the present invention, further comprises: 0 to 20 wt % (preferably, 0.1 to 20 wt %; more preferably, 0.5 to 10 wt %; most preferably, 1 to 5 wt %), based on the weight of the aqueous cleaning formulation, of a chelating agent, wherein the chelating agent is selected from the group consisting of ethylenediamine tetraacetic acid; ethylenediamine triacetic acid; ethylenediamine tetrapropionic acid; diethylenetriamine pentaacetic acid; nitrilotriacetic acid; oxydisuccinic acid; iminodisuccinic acid; benzene hexacarboxylic acid; poly(meth)acrylic acid, polyacrylic acid/polymethacrylic acid copolymers; benzene polycarboxylic acids; gluconic acid; sulfamic acid; oxalic acid; phosphoric acid; phosphonic acid; organic phosphonic acids; acetic acid; citric acid; sodium, potassium, lithium, ammonium and substituted ammonium salts thereof; and mixtures thereof.

Preferably, the aqueous cleaning formulation of the present invention, further comprises: 0 to 20 wt % (preferably, 0.1 to 20 wt %; more preferably, 0.5 to 10 wt %; most preferably, 1 to 5 wt %), based on the weight of the aqueous cleaning formulation, of a chelating agent, wherein the chelating agent is selected from the group consisting of (3-hydroxypropyl)iminodiacetic acid, (2-hydroxypropyl)iminodiacetic acid, glyceryliminodiacetic acid, dihydroxyisopropyliminodiacetic acid, methyliminodiaceticacid, 2-methoxyethyliminodiacetic acid, amidoiminodiacetic acid, acetamidoiminodiacetic acid, 3-methoxypropyliminodiacetic acid, tris(hydroxymethyl)methyliminodiacetic acid, ethylenediaminetetraacetic acid, salts thereof (preferably, sodium, potassium, lithium, ammonium and substituted ammonium salts thereof) and mixtures thereof.

Preferably, the aqueous cleaning formulation of the present invention, further comprises: 0 to 20 wt % (preferably, 0.1 to 20 wt %; more preferably, 0.5 to 10 wt %; most preferably, 1 to 5 wt %), based on the weight of the aqueous cleaning formulation, of a chelating agent, wherein the chelating agent includes tetrasodium ethylenediaminetetraacetate. More preferably, the aqueous cleaning formulation of the present invention, further comprises: 0 to 20 wt % (preferably, 0.1 to 20 wt %; more preferably, 0.5 to 10 wt %; most preferably, 1 to 5 wt %), based on the weight of the aqueous cleaning formulation, of a chelating agent, wherein the chelating agent is tetrasodium ethylenediaminetetraacetate.

Preferably, the aqueous cleaning formulation of the present invention, further comprises: 0 to 10 wt % (preferably, 0.1 to 10 wt %; more preferably, 0.5 to 7.5 wt %; most preferably, 1 to 5 wt %), based on the weight of the aqueous cleaning formulation, of a hydrotrope. More preferably, the aqueous cleaning formulation of the present invention, further comprises: 0 to 10 wt % (preferably, 0.1 to 10 wt %; more preferably, 0.5 to 7.5 wt %; most preferably, 1 to 5 wt %), based on the weight of the aqueous cleaning formulation, of a hydrotrope; wherein the hydrotrope is selected from the group consisting of urea; monoethanolamine; diethanolamine; triethanolamine; and calcium, sodium, potassium, ammonium and alkanol ammonium salts of xylene sulfonic acid, toluene sulfonic acid, ethylbenzene sulfonic acid and cumene sulfonic acid; and mixtures thereof. Still more preferably, the aqueous cleaning formulation of the present invention, further comprises: 0 to 10 wt % (preferably, 0.1 to 10 wt %; more preferably, 0.5 to 7.5 wt %; most preferably, 1 to 5 wt %), based on the weight of the aqueous cleaning formulation, of a hydrotrope; wherein the hydrotrope is selected from the group consisting of sodium toluene sulfonate, potassium toluene sulfonate, sodium xylene sulfonate, ammonium xylene sulfonate, potassium xylene sulfonate, calcium xylene sulfonate, sodium cumene sulfonate, ammonium cumene sulfonate and mixtures thereof. Yet still more preferably, the aqueous cleaning formulation of the present invention, further comprises: 0 to 10 wt % (preferably, 0.1 to 10 wt %; more preferably, 0.5 to 7.5 wt %; most preferably, 1 to 5 wt %), based on the weight of the aqueous cleaning formulation, of a hydrotrope;

wherein the hydrotrope includes sodium xylene sulfonate. Most preferably, the aqueous cleaning formulation of the present invention, further comprises: 0 to 10 wt % (preferably, 0.1 to 10 wt %; more preferably, 0.5 to 7.5 wt %; most preferably, 1 to 5 wt %), based on the weight of the aqueous cleaning formulation, of a hydrotrope; wherein the hydrotrope is sodium xylene sulfonate.

Preferably, the aqueous cleaning formulation of the present invention, further comprises: 0 to 10 wt % (preferably, 0.01 to 10 wt %; more preferably, 1 to 8 wt %; most preferably, 2.5 to 7.5 wt %), based on the weight of the aqueous cleaning formulation, of an organic solvent. Preferably, the aqueous cleaning formulation of the present invention, further comprises: 0 to 10 wt % (preferably, 0.01 to 10 wt %; more preferably, 1 to 8 wt %; most preferably, 2.5 to 7.5 wt %), based on the weight of the aqueous cleaning formulation, of an organic solvent; wherein the organic solvent is miscible with water. More preferably, the aqueous cleaning formulation of the present invention, further comprises: 0.01 to 10 wt % (preferably, 1 to 8 wt %; more preferably, 2.5 to 7.5 wt %), based on the weight of the aqueous cleaning formulation, of an organic solvent; wherein the organic solvent is selected from the group consisting of an aliphatic alcohol (e.g., $C_{1-6}$ alkanols, $C_{1-6}$ alkyl diols); a monoalkylene glycol ether (e.g., ethylene glycol propyl ether, ethylene glycol n-butyl ether, ethylene glycol t-butyl ether, propylene glycol propyl ether, propylene glycol n-butyl ether, propylene glycol t-butyl ether, propylene glycol methyl ether acetate, propylene glycol diacetate); a polyalkylene glycol ether (e.g., diethylene glycol ethyl ether, diethylene glycol propyl ether, diethylene glycol n-butyl ether, diethylene glycol t-butyl ether, diethylene glycol hexyl ether, dipropylene glycol methyl ether, dipropylene glycol ethyl ether, dipropylene glycol propyl ether, dipropylene glycol n-butyl ether, dipropylene glycol t-butyl ether, dipropylene glycol phenyl ether, dipropylene glycol methyl ether acetate, tripropylene glycol methyl ether, tripropylene glycol ethyl ether, tripropylene glycol propyl ether, tripropylene glycol n-butyl ether, tripropylene glycol t-butyl ether) and mixtures thereof. Still more preferably, the aqueous cleaning formulation of the present invention, further comprises: 0.01 to 10 wt % (preferably, 1 to 8 wt %; more preferably, 2.5 to 7.5 wt %), based on the weight of the aqueous cleaning formulation, of an organic solvent; wherein the organic solvent is selected from the group consisting of isopropanol, ethanol, 2-(2-butoxyethoxy)ethanol, ethylene glycol butyl ether, propylene glycol methyl ether, propylene glycol propyl ether, propylene glycol t-butyl ether, dipropylene glycol methyl ether, dipropylene glycol propyl ether, dipropylene glycol n-butyl ether and mixtures thereof. Yet more preferably, the aqueous cleaning formulation of the present invention, further comprises: 0.01 to 10 wt % (preferably, 1 to 8 wt %; more preferably, 2.5 to 7.5 wt %), based on the weight of the aqueous cleaning formulation, of an organic solvent; wherein the organic solvent includes dipropylene glycol methyl ether. Most preferably, the aqueous cleaning formulation of the present invention, further comprises: 0.01 to 10 wt % (preferably, 1 to 8 wt %; more preferably, 2.5 to 7.5 wt %), based on the weight of the aqueous cleaning formulation, of an organic solvent; wherein the organic solvent is dipropylene glycol methyl ether.

Preferably, the aqueous cleaning formulation of the present invention, further comprises 0 to 50 wt %, based on the weight of the aqueous cleaning formulation, of an additive. Preferably, the aqueous cleaning formulation of the present invention, further comprises 0 to 50 wt %, based on the weight of the aqueous cleaning formulation, of an additive selected from the group consisting of a salt, a builder, an enzyme, a corrosion inhibitor, an acid, a bleaching agent, an abrasive and mixtures thereof.

Preferably, the aqueous cleaning formulation of the present invention, further comprises 0 to 20 wt % (preferably, 0.1 to 20 wt %; more preferably, 0.1 to 10 wt %), based on the weight of the aqueous cleaning formulation, of a salt. More preferably, the aqueous cleaning formulation of the present invention, further comprises 0 to 20 wt % (preferably, 0.1 to 20 wt %; more preferably, 0.1 to 10 wt %), based on the weight of the aqueous cleaning formulation, of a salt; wherein the salt is selected from the group consisting of alkali metal halide salts (e.g., sodium chloride, potassium chloride); ammonium salts; nitrates; sulfates; nitrites and mixtures thereof.

Preferably, the aqueous cleaning formulation of the present invention, further comprises 0 to 50 wt % (preferably, 0.1 to 30 wt %; more preferably, 0.1 to 15 wt %), based on the weight of the aqueous cleaning formulation, of a builder. More preferably, the aqueous cleaning formulation of the present invention, further comprises 0 to 20 wt % (preferably, 0.1 to 20 wt %; more preferably, 0.1 to 10 wt %), based on the weight of the aqueous cleaning formulation, of a builder; wherein the builder is selected from the group consisting of inorganic builders (e.g., tripolyphosphate, pyrophosphate); alkali metal carbonates; borates; bicarbonates; hydroxides; zeolites; citrates; polycarboxylates; monocarboxylates; aminotrismethylenephosphonic acid; salts of aminotrismethylenephosphonic acid; hydroxyethanediphosphonic acid; salts of hydroxyethanediphosphonic acid; diethylenetriaminepenta(methylenephosphonic acid); salts of diethylenetriaminepenta(methylenephosphonic acid); ethylenediaminetetraethylene-phosphonic acid; salts of ethylenediaminetetraethylene-phosphonic acid; oligomeric phosphonates; polymeric phosphonates; mixtures thereof.

Preferably, the aqueous cleaning formulation of the present invention, further comprises 0 to 20 wt % (preferably, 0.1 to 20 wt %; more preferably, 0.1 to 10 wt %), based on the weight of the aqueous cleaning formulation, of a corrosion inhibitor. More preferably, the aqueous cleaning formulation of the present invention, further comprises 0 to 20 wt % (preferably, 0.1 to 20 wt %; more preferably, 0.1 to 10 wt %), based on the weight of the aqueous cleaning formulation, of a corrosion inhibitor; wherein the corrosion inhibitor is selected from the group consisting of sodium silicate, sodium disilicate, sodium metasilicate and mixtures thereof.

Preferably, the aqueous cleaning formulation of the present invention, further comprises 0 to 10 wt % (preferably, 1 to 5 wt %; more preferably, 2 to 4 wt %), based on the weight of the aqueous cleaning formulation, of an acid. More preferably, the aqueous cleaning formulation of the present invention, further comprises 0 to 10 wt % (preferably, 1 to 5 wt %; more preferably, 2 to 4 wt %), based on the weight of the aqueous cleaning formulation, of an acid; wherein the acid is selected from the group consisting of organic carboxylic acids and salts thereof (e.g., $C_{3-9}$ organic carboxylic acids such as gluconic acid, lactic acid, citric acid, glycolic acid, acetic acid, propionic acid, succinic acid, glutaric acid, adipinic acid, butanedioic acid, isoascorbic acid, ascorbatic acid, tatric acid).

Preferably, the aqueous cleaning formulation of the present invention, further comprises 0 to 10 wt % (preferably, 1 to 5 wt %; more preferably, 2 to 4 wt %), based on the weight of the aqueous cleaning formulation, of a bleaching agent. More preferably, the aqueous cleaning formulation of the present invention, further comprises 0 to 10 wt % (preferably, 1 to 5 wt %; more preferably, 2 to 4 wt %), based on the weight of the aqueous cleaning formulation, of a bleaching agent; wherein the bleaching agent is selected from the group consisting of hydrogen peroxide and chlorine-generating substances (e.g., sodium hypochlorite, chloroisocyanurate).

Preferably, aqueous cleaning formulation of the present invention, further comprises a pH adjuster. Preferred pH adjusters include sodium hydroxide, potassium hydroxide, sodium carbonate, potassium carbonate, monoethanolamine, triethanolamine, aminomethylpropanol, aminomethylpropanediol and trimethamine.

Preferably, the aqueous cleaning formulation of the present invention is provided as a single component system (i.e., as a single mixture of materials as opposed to a multi-component system, wherein some of the materials are maintained separately until dispensed for use).

Preferably, the method of cleaning a surface of the present invention, comprises providing a surface containing a material to be removed, providing an aqueous cleaning formulation of the present invention and contacting the surface with the aqueous cleaning formulation, whereby the material is removed from the surface.

Some embodiments of the present invention will now be described in detail in the following Examples.

Comparative Examples C1-C4 and Example 1: Hard Surface Cleaning Composition

Hard surface cleaning compositions of Comparative Examples C1-C4 and Example 1 were prepared by mixing together the components in the weight proportions noted in TABLE 1. Thyme oil was then titrated into a 100 g sample of each composition until turbidity was observed. The amount of thyme oil added is reported in TABLE 1.

TABLE 1

| | Comparative Examples | | | | |
|---|---|---|---|---|---|
| Ingredient | C1 (wt %) | C2 (wt %) | C3 (wt %) | C4 (wt %) | Ex. 1 (wt %) |
| Dipropylene glycol methyl ether solvent[1] | — | — | — | 5.0 | — |
| Nonionic secondary alcohol ethoxylate surfactant[2] | 7.5 | 7.5 | 7.5 | 7.5 | 7.5 |
| Dodecyl benzene sulfonic acid | 4.0 | 4.0 | 4.0 | 4.0 | 4.0 |
| Sodium xylene sulfonate | 2.0 | 2.0 | 2.0 | 2.0 | 2.0 |
| Tetrasodium ethylene diamine tetra acetate | 2.0 | 2.0 | 2.0 | 2.0 | 2.0 |
| PEG-40 hydrogenated castor oil[3] | — | — | 2.0 | 2.0 | 2.0 |
| Polyethylene glycol phenyl ether[4] | — | 5 | — | — | 5.0 |
| Deionized water | 84.5 | 79.5 | 82.5 | 77.5 | 77.5 |
| Thyme Oil | 2.17 g | 4.99 g | 2.37 g | 4.07 g | 6.78 g |

[1]Dowanol™ DPM glycol ether solvent available from The Dow Chemical Company
[2]Tergitol™ 15-S-15 surfactant available from The Dow Chemical Company
[3]Cremophor® RH 40 PEG-40 hydrogenated castor oil available from BASF
[4]Dowanol™ EPh6 glycol ether with $C_6H_5(OCH_2CH_2)_6OH$ as the average component available from The Dow Chemical Company

Comparative Examples C5-C9 and Example 2: Hard Surface Cleaning Composition

Hard surface cleaning compositions of Comparative Examples C5-C9 and Example 2 were prepared by mixing together the components in the weight proportions noted in TABLE 2. Lavender oil was then titrated into a 100 g sample of each composition until turbidity was observed. The amount of lavender oil added is reported in TABLE 2.

TABLE 2

| | Comparative Examples | | | | | |
|---|---|---|---|---|---|---|
| Ingredient | C5 (wt %) | C6 (wt %) | C7 (wt %) | C8 (wt %) | C9 (wt %) | Ex. 2 (wt %) |
| Dipropylene glycol methyl ether solvent[1] | — | — | — | 5.0 | 5.0 | — |
| Nonionic secondary alcohol ethoxylate surfactant[2] | 7.5 | 7.5 | 7.5 | 7.5 | 7.5 | 7.5 |
| Dodecyl benzene sulfonic acid | 4.0 | 4.0 | 4.0 | 4.0 | 4.0 | 4.0 |
| Sodium xylene sulfonate | 2.0 | 2.0 | 2.0 | 2.0 | 2.0 | 2.0 |
| Tetrasodium ethylene diamine tetra acetate | 2.0 | 2.0 | 2.0 | 2.0 | 2.0 | 2.0 |
| PEG-40 hydrogenated castor oil[3] | — | — | 2.0 | 2.0 | — | 2.0 |
| Polyethylene glycol phenyl ether[4] | — | 5 | — | — | — | 5.0 |
| Deionized water | 84.5 | 79.5 | 82.5 | 77.5 | 79.5 | 77.5 |
| Lavender Oil | 5.39 g | 5.84 g | 6.63 g | 7.58 g | 5.75 g | 8.00 g |

[1]Dowanol™ DPM glycol ether solvent available from The Dow Chemical Company
[2]Tergitol™ 15-S-15 surfactant available from The Dow Chemical Company
[3]Cremophor® RH 40 PEG-40 hydrogenated castor oil available from BASF
[4]Dowanol™ EPh6 glycol ether with $C_6H_5(OCH_2CH_2)_6OH$ as the average component available from The Dow Chemical Company

Comparative Examples C10-C14 and Example 3: Hard Surface Cleaning Composition Hard surface cleaning compositions of Comparative Examples C10-C14 and Example 3 were prepared by mixing together the components in the weight proportions noted in TABLE 3. Rosemary oil was then titrated into a 100 g sample of each composition until turbidity was observed. The amount of rosemary oil added is reported in TABLE 3.

TABLE 3

| Ingredient | C10 (wt %) | C11 (wt %) | C12 (wt %) | C13 (wt %) | C14 (wt %) | Ex. 3 (wt %) |
|---|---|---|---|---|---|---|
| Dipropylene glycol methyl ether solvent[1] | — | — | — | 5.0 | 5.0 | — |
| Nonionic secondary alcohol ethoxylate surfactant[2] | 7.5 | 7.5 | 7.5 | 7.5 | 7.5 | 7.5 |
| Dodecyl benzene sulfonic acid | 4.0 | 4.0 | 4.0 | 4.0 | 4.0 | 4.0 |
| Sodium xylene sulfonate | 2.0 | 2.0 | 2.0 | 2.0 | 2.0 | 2.0 |
| Tetrasodium ethylene diamine tetra acetate | 2.0 | 2.0 | 2.0 | 2.0 | 2.0 | 2.0 |
| PEG-40 hydrogenated castor oil[3] | — | — | 2.0 | 2.0 | — | 2.0 |
| Polyethylene glycol phenyl ether[4] | — | 5 | — | — | — | 5.0 |
| Deionized water | 84.5 | 79.5 | 82.5 | 77.5 | 79.5 | 77.5 |
| Rosemary Oil | 0.30 g | 0.50 g | 0.50 g | 0.60 g | 0.50 g | 0.79 g |

[1]Dowanol™ DPM glycol ether solvent available from The Dow Chemical Company
[2]Tergitol™ 15-S-15 surfactant available from The Dow Chemical Company
[3]Cremophor® RH 40 PEG-40 hydrogenated castor oil available from BASF
[4]Dowanol™ EPh6 glycol ether with C$_6$H$_5$(OCH$_2$CH$_2$)$_6$OH as the average component available from The Dow Chemical Company

Comparative Examples C15-C19 and Example 4: Hard Surface Cleaning Composition Hard surface cleaning compositions of Comparative Examples C15-C19 and Example 4 were prepared by mixing together the components in the weight proportions noted in TABLE 4. The turbidity of each composition was measured via the grayscale intensity of the sample in a Kimble™ Titeseal™ 1 mL shell vials against a black background with a scale of 0 (clear) to 255 (turbid) as reported in TABLE 4.

Comparative Examples C20-C24 and Example 5: Hard Surface Cleaning Composition Hard surface cleaning compositions of Comparative Examples C20-C24 and Example 5 were prepared by mixing together the components in the weight proportions noted in TABLE 5. The turbidity of each composition was measured as reported in TABLE 5. The turbidity of each composition was measured via the grayscale intensity of the sample in a Kimble™ Titeseal™ 1 mL shell vials against a black background with a scale of 0 (clear) to 255 (turbid) as reported in TABLE 5.

TABLE 4

| Ingredient | C15 (wt %) | C16 (wt %) | C17 (wt %) | C18 (wt %) | C19 (wt %) | Ex. 4 (wt %) |
|---|---|---|---|---|---|---|
| Dipropylene glycol methyl ether solvent[1] | — | — | — | 2.5 | 5.0 | — |
| Nonionic secondary alcohol ethoxylate surfactant[2] | 7.5 | 7.5 | 7.5 | 7.5 | 7.5 | 7.5 |
| Dodecyl benzene sulfonic acid | 4.0 | 4.0 | 4.0 | 4.0 | 4.0 | 4.0 |
| Sodium xylene sulfonate | 2.0 | 2.0 | 2.0 | 2.0 | 2.0 | 2.0 |
| Tetrasodium ethylene diamine tetra acetate | 2.0 | 2.0 | 2.0 | 2.0 | 2.0 | 2.0 |
| PEG-20 castor oil[3] | — | — | 5.0 | 2.5 | — | 2.5 |
| Polyethylene glycol phenyl ether[4] | — | 5.0 | — | — | — | 2.5 |
| Deionized water | 81.5 | 76.5 | 76.5 | 76.5 | 76.5 | 76.5 |
| D-Limonene | 3.0 | 3.0 | 3.0 | 3.0 | 3.0 | 3.0 |
| Turbidity | 35 | 33 | 26 | 39 | 30 | 14 |

[1]Dowanol™ DPM glycol ether solvent available from The Dow Chemical Company
[2]Tergitol™ 15-S-15 surfactant available from The Dow Chemical Company
[3]Tergitol™ Eco-20 caster oil derivative available from The Dow Chemical Company
[4]Dowanol™ EPh6 glycol ether with C$_6$H$_5$(OCH$_2$CH$_2$)$_6$OH as the average component available from The Dow Chemical Company

TABLE 5

| Ingredient | C20 (wt %) | C21 (wt %) | C22 (wt %) | C23 (wt %) | C24 (wt %) | Ex. 5 (wt %) |
|---|---|---|---|---|---|---|
| Dipropylene glycol methyl ether solvent[1] | — | — | — | 2.5 | 5.0 | — |
| Nonionic secondary alcohol ethoxylate surfactant[2] | 7.5 | 7.5 | 7.5 | 7.5 | 7.5 | 7.5 |
| Dodecyl benzene sulfonic acid | 4.0 | 4.0 | 4.0 | 4.0 | 4.0 | 4.0 |
| Sodium xylene sulfonate | 2.0 | 2.0 | 2.0 | 2.0 | 2.0 | 2.0 |
| Tetrasodium ethylene diamine tetra acetate | 2.0 | 2.0 | 2.0 | 2.0 | 2.0 | 2.0 |
| PEG-20 castor oil[3] | — | — | 5.0 | 2.5 | — | 2.5 |
| Polyethylene glycol phenyl ether[4] | — | 5.0 | — | — | — | 2.5 |
| Deionized water | 81.5 | 76.5 | 76.5 | 76.5 | 76.5 | 76.5 |
| α-pinene | 3.0 | 3.0 | 3.0 | 3.0 | 3.0 | 3.0 |
| Turbidity | 51 | 51 | 35 | 53 | 45 | 17 |

[1]Dowanol™ DPM glycol ether solvent available from The Dow Chemical Company
[2]Tergitol™ 15-S-15 surfactant available from The Dow Chemical Company
[3]Tergitol™ Eco-20 caster oil derivative available from The Dow Chemical Company
[4]Dowanol™ EPh6 glycol ether with $C_6H_5(OCH_2CH_2)_6OH$ as the average component available from The Dow Chemical Company

We claim:

1. An aqueous cleaning formulation, comprising:
   a water;
   an essential oil, wherein the essential oil comprises 50 to 100 wt % of one organic component;
   a derivative of castor oil having a formula selected from formula I and formula II

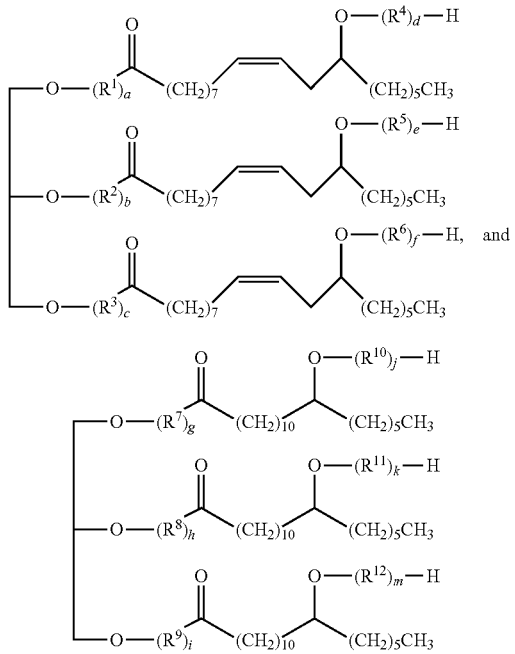

wherein $R^1$, $R^2$, $R^3$, $R^4$, $R^5$, $R^6$, $R^7$, $R^8$, $R^9$, $R^{10}$, $R^{11}$ and $R^{12}$ are each independently selected from the group consisting of a —$CH_2CH_2O$— group, a —$CH_2CH_2CH_2O$— group, a —$CH_2CH_2CH_2CH_2O$— group, a —$CH(CH_3)CH_2O$— group, a —$CH_2CH(CH_3)O$— group, a —$CH(CH_3)CH_2CH_2O$— group, a —$CH_2CH(CH_3)CH_2O$— group and a —$CH_2CH_2CH(CH_3)O$— group each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250;
   an ethoxylated phenol having formula III

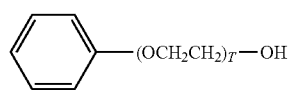

wherein T is an average of 3 to 8; and
   a cleaning surfactant.

2. The aqueous cleaning formulation of claim 1, wherein the essential oil is selected from the group consisting of lavender oil, rosemary oil, thyme oil, D-limonene, α-pinene and mixtures thereof.

3. The aqueous cleaning formulation of claim 1, further comprising 0.1 to 20 wt %, based on the weight of the aqueous cleaning formulation, of a chelating agent.

4. The aqueous cleaning formulation of claim 1, further comprising 0.1 to 10 wt %, based on the weight of the aqueous cleaning formulation, of a hydrotrope.

5. The aqueous cleaning formulation of claim 1, further comprising 0.01 to 10 wt %, based on the weight of the aqueous cleaning formulation, of an organic solvent.

6. The aqueous cleaning formulation of claim 1, further comprising
   0.1 to 15 wt %, based on weight of the aqueous cleaning formulation of the cleaning surfactant, wherein the cleaning surfactant includes a non-ionic surfactant;
   0.1 to 20 wt %, based on the weight of the aqueous cleaning formulation, of a chelating agent;
   0.1 to 10 wt %, based on the weight of the aqueous cleaning formulation, of a hydrotrope; and
   0.01 to 10 wt %, based on the weight of the aqueous cleaning formulation, of an organic solvent.

7. The aqueous cleaning formulation of claim 6, wherein the essential oil is selected from the group consisting of lavender oil, rosemary oil and thyme oil.

8. The aqueous cleaning formulation of claim 7, wherein the aqueous cleaning formulation contains
- 10 to 99 wt %, based on the weight of the aqueous cleaning formulation, of the water;
- 7.6 to 10 wt %, based on the weight of the aqueous cleaning formulation, of the essential oil, wherein the essential oil is lavender oil;
- 0.01 to 25 wt %, based on the weight of the aqueous cleaning formulation, of the derivative of castor oil, wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250;
- 0.01 to 30 wt %, based on the weight of the aqueous cleaning formulation, of the ethoxylated phenol, wherein T is an average of 3 to 8;
- 0.1 to 15 wt %, based on weight of the aqueous cleaning formulation of the cleaning surfactant, wherein the cleaning surfactant includes a non-ionic surfactant;
- 0.1 to 20 wt %, based on the weight of the aqueous cleaning formulation, of a chelating agent;
- 0.1 to 10 wt %, based on the weight of the aqueous cleaning formulation, of a hydrotrope; and
- 0.01 to 10 wt %, based on the weight of the aqueous cleaning formulation, of an organic solvent.

9. The aqueous cleaning formulation of claim 7, wherein the aqueous cleaning formulation contains
- 10 to 99 wt %, based on the weight of the aqueous cleaning formulation, of the water;
- 0.61 to 1 wt %, based on the weight of the aqueous cleaning formulation, of the essential oil, wherein the essential oil is rosemary oil;
- 0.01 to 25 wt %, based on the weight of the aqueous cleaning formulation, of the derivative of castor oil, wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250;
- 0.01 to 30 wt %, based on the weight of the aqueous cleaning formulation, of the ethoxylated phenol, wherein T is an average of 3 to 8;
- 0.1 to 15 wt %, based on weight of the aqueous cleaning formulation of the cleaning surfactant, wherein the cleaning surfactant includes a non-ionic surfactant;
- 0.1 to 20 wt %, based on the weight of the aqueous cleaning formulation, of a chelating agent;
- 0.1 to 10 wt %, based on the weight of the aqueous cleaning formulation, of a hydrotrope; and
- 0.01 to 10 wt %, based on the weight of the aqueous cleaning formulation, of an organic solvent.

10. The aqueous cleaning formulation of claim 7, wherein the aqueous cleaning formulation contains
- 10 to 99 wt %, based on the weight of the aqueous cleaning formulation, of the water;
- 5 to 10 wt %, based on the weight of the aqueous cleaning formulation, of the essential oil, wherein the essential oil is thyme oil;
- 0.01 to 25 wt %, based on the weight of the aqueous cleaning formulation, of the derivative of castor oil, wherein $R^1$, $R^2$, $R^3$, $R^4$, $R^5$, $R^6$, $R^7$, $R^8$, $R^9$, $R^{10}$, $R^{11}$, and $R^{12}$ are each a —$CH_2CH_2O$— group; wherein a, b, c, d, e, f, g, h, i, j, k and m are each independently a number of 0 to 250; wherein the average sum of a+b+c+d+e+f is 1 to 250; wherein the average sum of g+h+i+j+k+m is 1 to 250;
- 0.01 to 30 wt %, based on the weight of the aqueous cleaning formulation, of the ethoxylated phenol, wherein T is an average of 3 to 8;
- 0.1 to 15 wt %, based on weight of the aqueous cleaning formulation of the cleaning surfactant, wherein the cleaning surfactant includes a non-ionic surfactant;
- 0.1 to 20 wt %, based on the weight of the aqueous cleaning formulation, of a chelating agent;
- 0.1 to 10 wt %, based on the weight of the aqueous cleaning formulation, of a hydrotrope; and
- 0.01 to 10 wt %, based on the weight of the aqueous cleaning formulation, of an organic solvent.

\* \* \* \* \*